United States Patent [19]
Khan et al.

[11] Patent Number: 4,789,549
[45] Date of Patent: Dec. 6, 1988

[54] SUSTAINED RELEASE DOSAGE FORMS

[75] Inventors: Sadath U. Khan, Mine Hill; Pijush K. Chakraborty, Maplewood; Albert T. Grabowski, Dover, all of N.J.; Reginald Phillips, Coral Spring, Fla.

[73] Assignee: Warner-Lambert Company, Morris Plains, N.J.

[21] Appl. No.: 23,424

[22] Filed: Mar. 9, 1987

[51] Int. Cl.$^4$ .......................... A61K 9/36; A61K 9/14
[52] U.S. Cl. .................................. 424/480; 424/482; 424/486; 424/488
[58] Field of Search ............... 424/468, 469, 470, 472, 424/473, 480, 482, 486, 488; 427/9

[56] References Cited

U.S. PATENT DOCUMENTS

| | | | |
|---|---|---|---|
| 4,369,172 | 1/1983 | Schor et al. | 424/473 X |
| 4,389,393 | 6/1983 | Schor et al. | 424/469 |
| 4,443,428 | 4/1984 | Oshlack et al. | 424/468 X |
| 4,663,150 | 5/1987 | Panoz et al. | 424/494 |
| 4,716,040 | 12/1987 | Panoz | 424/459 |

FOREIGN PATENT DOCUMENTS 2068226A 12/1980 United Kingdom.

Primary Examiner—Michael Lusignan
Attorney, Agent, or Firm—Elizabeth M. Anderson

[57] ABSTRACT

A unique sustained release dosage form which prevents the tendency of an initial surge of medicament in the first hour of administration. The control is by a porous membrane coating. The amount of initial release can be varied by varying the proportions of the components of the coatings.

7 Claims, 2 Drawing Sheets

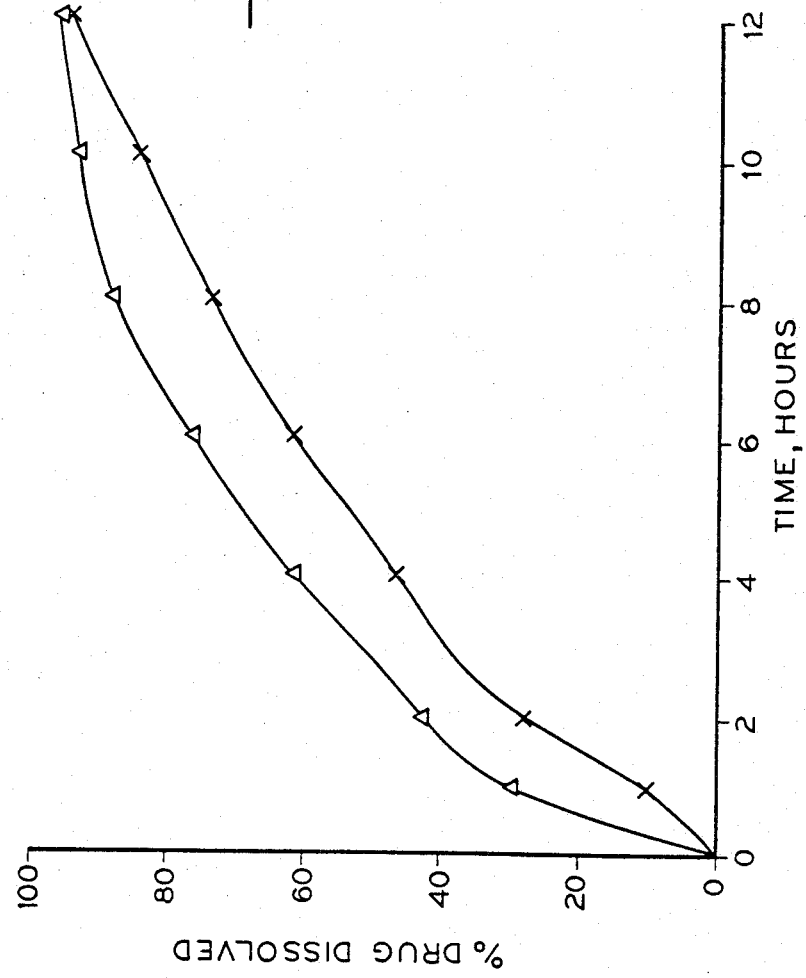

SUSTAINED RELEASE DOSAGE FORMS

BACKGROUND OF THE INVENTION

The preparation of sustained release dosage forms which utilize water miscible drugs as substrates have long been plagued by problems. One major problem has been the tendency of such drugs to "dump" or "surge" into the body during the first hour or two after an oral dosage form containing them is swallowed. The problem is caused by their affinity for aqueous environments.

In the present invention certain readily water soluble drugs are administered in unique slow-or substained-release oral, vaginal, or rectal dosage forms. These dosage forms comprise a novel two-part system, a core or inner portion in which the drug is dispersed in a matrix of a water soluble polymer and an outer portion, which is a semi-permeable membrane containing a solvent. The solvent is a water-based polymeric coating solution. The solubility of the polymeric component is pH dependent.

U.S. Pat. Nos. 4,369,172 and 4,389,393 show the use of hydroxypropyl-methylcellulose and another celluloic material in a carrier base for a dosage form.

U.S. Pat. No. 4,443,428 describes oral dosage forms which contain a wax matrix. British application 2,068,226A shows sustained release compositions containing disopyramide, glyceryl monostearate, castor sugar, polyvinyl pyrrolidine, magnesium stearate, and a coating of hydroxypropylmethyl cellulose, glucose, and propylene glycol.

SUMMARY

An object of the present invention is to provide an improved dosage form which has prolonged release of a medicament without the initial surge during the first hours of administration.

These improvements are found in a dosage form which has an inner portion of the medicament in a polymer matrix and an outer portion or coating which is a semi-permeable membrane.

BRIEF DESCRIPTION OF THE DRAWING

FIGS. 1 and 2 show comparative dissolution profiles of drugs.

DETAILED DESCRIPTION

Figure 1:
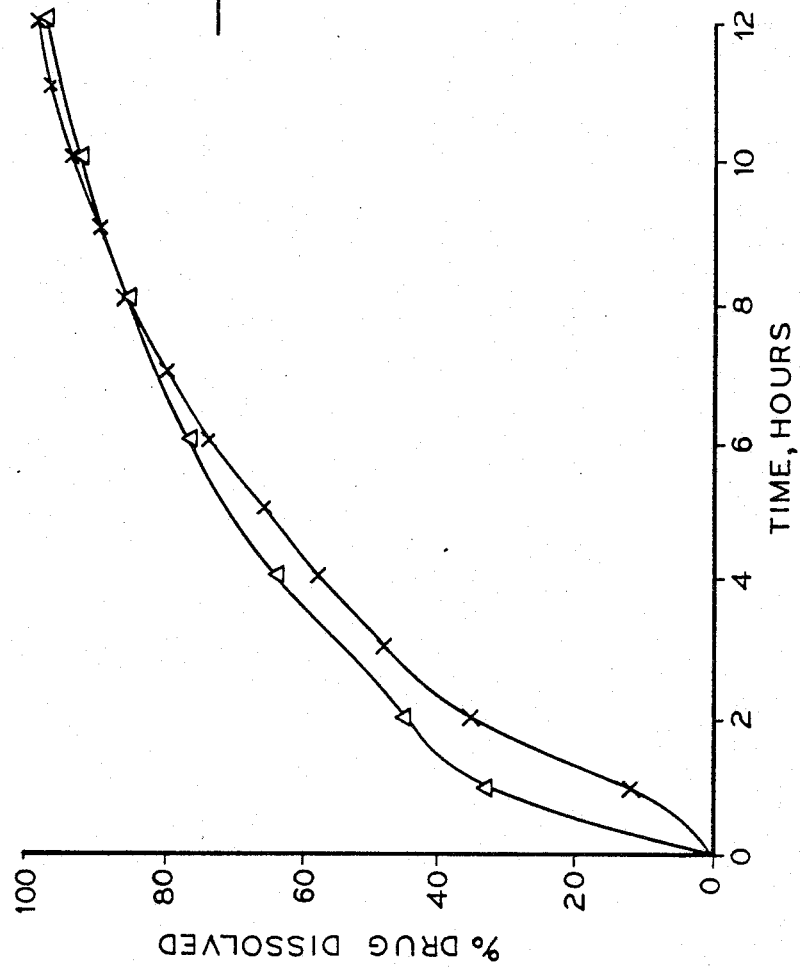

In the instant invention the tendency for an initial surge of medication resulting in the dissolution of the drug in substantially large amounts in the first hour than in subsequent hours has been overcome. A sustained release dosage form has been found to control the initial surge in the dissolution. The improvement of the present invention is shown in the profiles of sustained release action in FIGS. I and II below.

The dosage form consist of an inner core or portion which is a water-soluble medicament in a water soluble polymer matrix. This inner portion is coated with a semi-permeable membrane or outer portion. The dosage form comprises a therapeutically active medicament in a water soluble polymer matrix which comprises an inner core of the dosage form. This inner portion or core is coated with a semi-premeable membrane. The percent medicament to matrix can vary from about 90 to 10% to about 78 to 22%. Preferably the ratio is from about 88 to 12%.

The dosage form is water soluble at pHs of from about 1.2 to about 7.5. The preferred pH range is from about 4.5 to about 6.5.

The dosage form may be many as would occur to one skilled in the art. Preferably the form is a tablet. The form is for different routes of administration as would occur to a skilled practitioner. Preferable routes are oral, buiccal, sublinguial, vaginal, rectal, and the like. The medicament in the inner portion of the dosage form will be any drug which is water soluble and which benefits the patient by controlled release of the same. Such drugs are, for example; diphenhydramine hydrochloride, disopyramide phosphate, procainamide HCl, methyldopa, pseudoephedrine HCl, sodium meclofenamate.

Preferably the medicament is diphenhydramine hydrochloride, or disopyramide phosphate. The water soluble polymer matrix may be one that provides a gel-like layer under the action of water. Such matrices are: hydroxypropyl methylcellulose, hydroxyethyl cellulose, hydroxypropyl cellulose, or povidone. Preferred matrices are hydroxypropyl, methylcellulose, and hydroxethyl cellulose.

In one preferred embodiment, freely water soluble diphenhydramine hydrochloride is dispersed in a water soluble hydroxypropyl methylcellulose matrix to produce a core or inner portion. This core is then coated with composition (I), an aqueous coating solution consisting of a water soluble polymeric system containing a hydroxypropyl cellulose polymer (Klucel) and Aquateric ® (FMC, Philadelphia, Pa.) Aquateric ® contains about 70% cellulose acetate phthalate. The remainder of Aquateric ® is composed of polyoxypropylene, polyoxyethylene block copolymer and acetylated monoglycerides. Alternatively the core is coated with composition (II), a solvent coating solution consisting of a hydroxypropyl cellulose polymer and polyvinyl acetate phthalate in a suitable solvent such as acetone, SD 3A alcohol and water. The coating compositions are water soluble at pH's between about 4.5 and about 7.5. The final dosage form is a tablet having sustained release properties with no significant initial surge on dissolution.

In another preferred embodiment disopyramide phosphate is dispersed in a hydroxyethyl cellulose polymeric matrix to yield a core or inner portion. This core is then coated with a membrane as described above for either composition I or II. The product is a tablet showing sustained release with minimal surge initial dissolution.

The polymer matrix is one that provides a prolonged release of the medicament by forming a gel-like layer under the action of water. This layer retards the diffusion of the active ingredient from the dosage form. The initial dissolution is controlled by the porous membrane created by the dissolution of a water soluble polymer such as hydroxypropyl cellulose. The amount of the initial release of a medicament is controlled by varying the proportions of hydroxypropyl cellulose and cellulose acetate phthalate or polyvinyl acetate phthalate in the formulation.

Comparative dissolution profiles of drugs before and after coating is given in FIGS. 1 and 2 below. FIG. 1 shows the comparative dissolution profile of diphenydramine hydrochloride coated (x) and uncoated (Δ) tablets. The dissolution media in the first hour is simulated gastric fluid followed by simulated intestinal fluid. Other possible components are those that would occur to one skilled in the art.

The following illustrative embodiments of the present invention are non-limiting and variations thereof will be obvious to those skilled in the art.

TABLE I

Diphenhydramine Hydrochloride Tablet Formulation with Hydroxypropyl Methylcellulose

| | |
|---|---|
| Diphenhydramide HCl | 125.90% |
| Sterotex Powder HM | 10.30% |
| Ethylcellulose NF 10 cps | 5.52% |
| Alcohol SD 3A Anhydrous | q.s |
| Hydroxypropyl Methylcellulose 2910 USP | 24.14% |
| Calcium Sulfate Anhydrous NF | 31.90% |
| Syloid 244 Silica Gel | 0.52% |
| Magnesium Stearate, NF | 1.72% |

TABLE II

Disopyramide Phosphate Tablet Formulation with Hydroxyethyl Cellulose

| | |
|---|---|
| Disopyramide Phosphate | 64.50% |
| Hydroxyethyl Cellulose Type H | 28.50% |
| Confectioners Sugar USP | 4.50% |
| Silicon dioxide NF | 0.50% |
| Calcium Stearate NF | 2.00% |
| Purified Water USP | q.s. |

TABLE III

Aqueous Coating Solution to Control The Initial Surge in Dissolution

| | |
|---|---|
| Hydroxypropyl Cellulose NF | 1.40% |
| Polyethylene Glycol 3350 NF | 1.00% |
| Aquateric Powder ® | 13.40% |
| Ethyl Phthalate | 4.00% |
| Antifoam AF Emulsion | 0.20% |
| Purified Water USP | 80.00% |

TABLE IV

Solvent Coating Solution to Control The Initial Surge in Dissolution

| | |
|---|---|
| Hydroxypropyl Cellulose NF | 5.00% |
| Stearic Acid NF | 0.30% |
| Polyvinyl Acetate Phthalate Powder NF | 5.00% |
| Triethyl Citrate FCC | 1.20% |
| Mistron Spray Talc | 4.00% |
| Purified Water USP | 5.50% |
| Acetone USP | 2.10% |
| Alcohol SD 3A, Anhydrous | 76.90% |

In the claims:

1. A sustained release dosage form comprising an effective amount of a water-soluble therapeutically active medicament in a water soluble polymer matrix which matrix is coated with a semipermeable membrane said coating consisting of effective amounts of
   (a) hydroxypropyl cellulose polymer and
   (b) cellulose acetate phthalate with polyoxpropylene polyoxyethylene block copolymer and acetylated monoglycerides, and said coating being water soluble at pHs between about 5.5 and about 6.5.

2. A dosage form according to claim 1 wherein the water soluble medicament is diphenhydramine hydrochloride and the polymer matrix is hydroxypropyl methylcellulose.

3. A dosage form according to claim 1 wherein the water soluble medicament is disopyramide phosphate and the polymer matrix is hydroxyethyl cellulose.

4. A dosage form according to claim 1 wherein the semipermeable membrane coating consists of a) hydroxypropyl cellulose and b) polyvinyl acetate phthalate.

5. A dosage form according to claim 1 wherein the percent of medicament to matrix is from about 90 to about 10.

6. The dosage form according to claim 1 which is a tablet.

7. The dosage form according to claim 1 wherein the therapeutically active medicament is diphenhydramine hydrochloride, disopyramide phosphate, procainamide, pseudoephedrine HCl, sodium meclofenamate, or methyldopa.

* * * * *